United States Patent [19]

Knowles et al.

[11] 4,075,005
[45] Feb. 21, 1978

[54] HERBICIDAL COMPOSITIONS

[75] Inventors: David Alan Knowles, Tonbridge; Clive Gilroy Robson, Staplehurst, both of England

[73] Assignee: Imperial Chemical Industries Limited, London, England

[21] Appl. No.: 757,912

[22] Filed: Dec. 27, 1976

[30] Foreign Application Priority Data

Jan. 20, 1976  United Kingdom ............... 2174/76

[51] Int. Cl.$^2$ ............................................. A01N 9/22
[52] U.S. Cl. ............................................ 71/94; 71/92; 71/DIG. 1
[58] Field of Search ........................... 71/94, 92, 113

[56] References Cited

U.S. PATENT DOCUMENTS 3,920,443  11/1975  Drewe et al. ........................... 71/94

OTHER PUBLICATIONS

The Merck Index–Seventh Edition, 1960, pp. 183, 184, 1086 and 1087.
Tung et al., Chem. Abst., vol. 67, (1967), 89968a.

*Primary Examiner*—Lewis Gotts
*Assistant Examiner*—Catherine L. Mills
*Attorney, Agent, or Firm*—Cushman, Darby & Cushman

[57] ABSTRACT

Herbicidal compositions containing as active ingredients quaternary bipyridylium herbicides and additionally containing as a safety factor, an odorant alkyl carboxylic acid such as valeric acid and butyric acid.

7 Claims, No Drawings

HERBICIDAL COMPOSITIONS

This invention relates to concentrated herbicidal compositions containing a herbicidal bipyridylium quaternary salt as an active ingredient.

Following the discovery of the insecticidal properties of DDT and the synthesis of the hormone type weedkillers exemplified by 2,4-dichlorophenoxyacetic acid, a large range of pesticides has been developed for agricultural use in the control of fungal and insect pests and weeds. While these substances are necessarily toxic to certain forms of life, when used with due care and in accordance with governmentally approved codes of practice, they present no hazard to human life. However, in spite of efforts to encourage those concerned with pesticides to adopt safe handling practices, instances of misuse of pesticides do occur. One particular unsafe practice in the case of liquid pesticides is for an operator to transfer a small amount of the concentrated pesticide to a domestic container such as a beverage bottle for subsequent use at home. The risk attached to this practice is of course that a child or incautious adult coming upon the bottle may swallow the contents with possibly serious consequences.

U.K. Patent Specification No. 1,406,881 discloses herbicidal compositions comprising an aqueous solution of a salt of a herbicidal bipyridylium quaternary cation and an odourant comprising the substance pyridine base which comprises a mixture of alkyl pyridines. The unpleasant smell of the odourant acts as a warning that the composition is not a beverage; with the consequential reduction in the likelihood of accidental swallowing of these herbicides in the circumstances described above.

The choice of an odourant for admixture with bipyridylium quaternary cation herbicides is greatly restricted by the exacting technical requirements which such an odourant must meet. For example, the odourant must be sufficiently soluble in concentrated bipyridylium solutions, it must be physically and chemically compatible with the bipyridylium cation, it must have sufficient stability on storage for long periods and it must possess an odour not to be confused with the characteristic odour of other commercial products.

The use of the substance pyridine based referred to hereinabove imposes a burden on the manufacturer since the composition of the pyridine base varies according to its source and it is necessary to monitor the composition to check that it meets with the appropriate standard. An odourant material available in substantially pure form would therefore be advantageous.

We have now discovered that by suitable alteration of the composition of a bipyridylium solution comprising an alkyl carboxylic acid as odourant, previously thought to be unsuitable, a composition having satisfactory deterrent properties can be obtained.

According to the present invention, there is provided a concentrated herbicidal composition comprising an aqueous solution having a pH not greater than 5, of a salt of a herbicidal bipyridylium quaternary cation and an odourant comprising an alkyl carboxylic acid. The unpleasant smell of the odourant acts as a warning that the composition is not a beverage.

By the term alkyl carboxylic acid is meant a compound of the formula RCOOH wherein R is a straight or branched chain alkyl group containing from three to five carbon atoms. Preferred alkyl carboxylic acids for use in the compositions of the invention are n-butyric acid (I) isobutyric acid (II) and n-valeric acid (III).

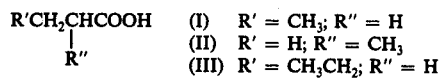

(I) $R' = CH_3; R'' = H$
(II) $R' = H; R'' = CH_3$
(III) $R' = CH_3CH_2; R'' = H$

Preferably the composition has a pH in the range 1 to 5.

Preferably the composition also comprises a surface-active agent. Preferred herbicidal bipyridylium quaternary salts for use in the compositions of the invention are those of the following formulae:

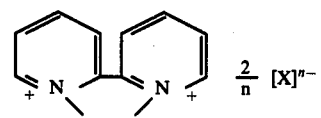

or

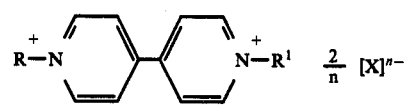

wherein R and $R^1$, which may be the same or different, stand for alkyl radicals of from 1 to 4 carbon atoms which may be substituted by hydroxyl, halogen, carboxyl, lower alkoxy, lower alkylcarbonyl, lower alkoxycarbonyl, carbamoyl or N-lower alkyl substituted carbamoyl; $[X]^{n-}$ represents an anion and $n$ is an integer from 1 to 4 inclusive. By lower alkoxy, alkoxycarbamoyl, alkylcarbonyl, or alkyl, is meant radicals containing an alkyl group of 1 to 4 carbon atoms; this definition applies in the claims at the end of this specification.

Particularly preferred herbicidal bipyridylium quaternary salts are those listed below:

1,1'-dimethyl-4,4'-bipyridylium di(methylsulphate) (paraquat methosulphate)
1,1'-ethylene-2,2'-bipyridylium dibromide (diquate dibromide)
1,1'-dimethyl-4,4'-bipyridylium dichloride (paraquat dichloride)
1,1'-di-2-hydroxyethyl-4,4'-bipyridylium dichloride
1-(2-hydroxyethyl-1'-methyl-4,4'-bipyridylium dichloride
1,1'-di-carbamoylmethyl-4,4'-bipyridylium dichloride
1,1'-bis-N,N-dimethylcarbamoylmethyl-4,4'-bipyridylium dichloride
1,1'-dimethyl-4,4'-bipyridylium sulphate (paraquat sulphate)
1,1'-bis- N,N-diethylcarbamoylmethyl-4,4'-bipyridylium dichloride
1,1-diacetonyl-4,4'-bipyridylium dichloride
1,1'-diethoxycarbonylmethyl-4,4'-bipyridylium dibromide
1,1'-diallyl-4,4'-bipyridylium dibromide The names in brackets alongside some of the compounds in the above list are the accepted common names for the cationic portion of these compounds. Thus 'paraquat' is the common name for the 1,1'-dimethyl-4,4'-bipyridylium cation. Paraquat is a more particularly preferred bipyridylium compound for use in the compositions of the invention.

Since the herbicidal effect of a bipyridylium quaternary cation is independent of the nature of the associated anion, the choice of the anion is a matter of convenience, depending, for example, on cost. Preferably the anion is one which gives rise to a salt of convenient water solubility. Examples of anions, which may be mono- or poly-valent, include acetate, benzenesulphonate, benzoate, bromate, bromide, butyrate, chlorate, chloride, citrate, formate, fluorosilicate, fumarate, fluoroborate, iodide, lactate, malate, maleate, methylsulphate, nitrate, propionate, phosphate, salicylate, sulphamate, succinate, sulphate, thiocyanate, tartrate, and p-toluenesulphonate. The salt of the herbicidal bipyridylium cation may be formed from a number of similar anions or mixtures of different ones. A salt having any particular desired anion may be prepared either by direct synthesis from reactants which include the desired anion, or by exchanging the anion of a previously prepared salt for the preferred anion by methods well known in the art, for example by passage of a solution of the previously prepared salt through an ion-exchange resin. For reasons of convenience the economy, the chloride anion is a particularly preferred anion.

Since the characteristic herbicidal activity of a salt of a herbicidal bipyridylium quaternary cation resides in the cation only, it is customary to quote concentrations of active ingredient and rates of application in terms of the amount of bipyridylium quaternary cation used, thus avoiding the inconvenience of having to quote different application rates for different salts of the same bipyridylium quaternary cation. Application rates and concentrations quoted in this specification therefore relate to the amount of herbicidal bipyridylium quaternary cation unless otherwise stated.

The amount of herbicidal bipyridylium quaternary cation present in the compositions of the invention is preferably from 0.5 to 3.0 pounds per Imperial gallon (50 grams to 300 grams per liter) and more preferably from 1.0 to 2.5 pounds per Imperial gallon (100 to 250 grams per liter).

Surface active agents may be cationic, non-ionic or anionic. Generally speaking cationic and non-ionic surface-active agents are preferred to anionic surface active agents for use in the compositions of the invention, since the latter may interact undesirably with the bipyridylium quaternary salt in the composition. Examples of non-ionic surface-active agents for use in the compositions of the invention include the condensation products of ethylene oxide with alkyl phenols such as octylphenol, nonylphenol and octylcresol. Other non-ionic agents are the partial esters derived from long chain fatty acids and hexitol anhydrides, for example sorbitan monolaurate; the condensation products of the said partial esters with ethylene oxide; and the lecithins. Examples of cationic surface-active agents include quaternary salts and condensates of ethylene oxide with amines, for example the substances sold under the Trade Mark "Ethomeen", "Ethoduomeen", "Duoquad" and "Arquad".

Particularly preferred surface-active agents are the combinations of surface-active agents described in U.K. Pat. No. 998,264 for use in formulations of herbicidal bipyridylium quaternary salts, which description is incorporated herein by reference.

The amount of surface-active agent present in the composition is preferably from 20 to 100 grams per liter of the composition.

The choice of an odourant for an aqueous composition comprising a herbicidal bipyridylium salt is by no means a simple matter. For reasons of economy in transport and storage it is desirable for the compositions to be sold in the form of a concentrate, which may be diluted with water as required to form a solution of suitable strength for application. Such concentrates may contain for example from 5 to 20% by weight of herbicidal bipyridylium quaternary cation. Many substances are not miscible with or soluble in solutions of bipyridylium salts of this concentration with the result that the excess of odourant floats on the surface of the concentrate. This results in uneven distribution of the odourant when the concentrate is re-packed into small containers from bulk. Insoluble substances are therefore unsuitable as odourants. Furthermore, the odourant must not react chemically with the active ingredient, or otherwise impair the herbicidal properties of the latter. Since many months may elapse between the formulation of the herbicidal concentrate and its use, it is essential for the odourant not to deteriorate on storage. Compositions according to the invention in 2 year storage tests have been found to maintain their repulsive smell.

Compositions according to the invention preferably contain from 0.5 to 5% by weight of the alkyl carboxylic acid used as the odourant. More preferably the amount of alkyl carboxylic acid used is from 1 to 4% by weight.

Due to their low pH, the formulations of our invention are corrosive. They must be handled with care, to avoid splashing of the eyes or skin, and they should not be allowed to come into contact with corrodeable metals prior to dilution.

The compositions according to the invention may also comprise coloured dyestuff or pigment compounds. Examples of such compounds for use in the practice of the invention are "Monastral Blue BNV Paste" and "Lissimine Turquoise VN 150".

EXAMPLE 1

This Example illustrates a composition according to the invention which comprises n-valeric acid 1% w/v as odourant in aqueous solution. The composition comprises the following ingredients.

| Ingredients | % w/v |
| --- | --- |
| Paraquat concentrate | x |
| Sodium metaborate | 1.3 |
| Sodium benzoate | 2.0 |
| Lissapol NX | 1.1 |
| DS 4392 | 4.1 |
| Silcolapse M5000 | 0.06 |
| n-valeric acid | 1.0 |
| Water to | 100 |
| (where x gives 200 ± 5 g/liter paraquat ion) | |
| pH 3.5 ± 0.5  Specific gravity 1.05 – 1.12 | |

Paraquat concentrate is a solution of paraquat dichloride containing 25 to 30% by weight of 1,1'-dimethyl-4,4'-bipyridylium cation. The amount specified in the table above was sufficient to give a composition containing 20% by weight of paraquat cation.

The pH was adjusted to pH 3.5 by the addition of concentrated hydrochloric acid.

"Lissapol" NX is a Trade Mark for a surface-active agent comprising a condensate of from 7 to 8 molar proportions of ethylene oxide with 1 molar proportion of p-nonylphenol.

DS 4392. This is a code number for a surface-active agent comprising a mixture of amines derived from soya bean fatty acids condensed with approximately 15 molar proportions of ethylene oxide.

"Silcolapse" is a Trade Mark for an anti-foaming agent comprising a silicone derivative.

The composition described above was prepared by simple agitation of the ingredients together.

EXAMPLE 2

This Example illustrates a composition according to the invention which comprises a concentrated aqueous solution with iso-butyric acid (4% w/v) as odourant. The composition comprises the following ingredients.

| Ingredients | | % w/v |
|---|---|---|
| Paraquat concentrate | | x |
| Sodium metaborate | | 1.3 |
| Sodium benzoate | | 2.0 |
| Lissapol NX | | 1.1 |
| DS 4392 | | 4.1 |
| Silcolapse M5000 | | 0.06 |
| Iso-butyric acid | | 4.0 |
| Water | to | 100 |
| (where x gives 200 ± 5 g/liter paraquat ion) | | |
| pH 3.5 ± 0.5   Specific gravity 1.05 – 1.12 | | |

The composition was prepared in the same way as in Example 1.

EXAMPLE 3

This Example illustrates a composition according to the invention which comprises a concentrated aqueous solution having n-butyric acid (4% w/v) as the odourant. The composition comprises the following ingredients.

| Ingredients | | % w/v |
|---|---|---|
| Paraquat concentrate | | x |
| Sodium metaborate | | 1.3 |
| Sodium benzoate | | 2.0 |
| Lissapol NX | | 1.1 |
| DS 4392 | | 4.1 |
| Silcolapse M5000 | | 0.06 |
| n-butyric acid | | 4.0 |
| Water | to | 100 |
| (where x gives 200 ± 5 g/liter paraquat ion) | | |
| pH 3.5 ± 0.5   Specific gravity 1.05 – 1.12 | | |

The composition was prepared in the same way as in Example 1.

EXAMPLE 4

This Example illustrates a composition according to the invention which comprises a concentrated aqueous solution having n-valeric acid (1% w/v) as the odourant. The composition comprises the following ingredients.

| Ingredient | | % w/v |
|---|---|---|
| Paraquat concentrate | | x |
| n-Valeric acid | | 1.0 |
| Water | to | 100 |
| (where x gives 200 ± 5 g/liter paraquat ion) | | |

-continued

| Ingredient | % w/v |
|---|---|
| pH 3.5 ± 0.5 | |

The composition was prepared in the same way as in Example 1.

We claim:

1. A concentrated herbicidal composition, comprising an aqueous solution having a pH not greater than 5, of a herbicidally effective amount of a salt of a herbicidal bipyridylium quaternary cation selected from the group consisting of compounds of the formula:

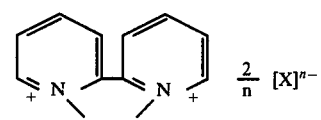

or

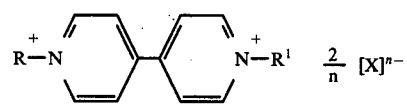

wherein R and $R^1$ are selected independently from the group consisting of alkyl radicals of from 1 to 4 carbon atoms and alkyl radicals of from 1 to 4 carbon atoms substituted by a radical selected from the group consisting of hydroxy, halogen, carboxyl, lower alkoxy, lower alkylcarbonyl, lower alkoxycarbonyl, carbamoyl or N-lower alkyl substituted carbamoyl; $[X]^{n-}$ represents an anion and $n$ is an integer of from 1 to 4 inclusive; together with an odourant having an unpleasant smell and comprising an alkyl carboxyl acid of the formula RCOOH wherein R is a straight or branched chain alkyl group containing from three to five carbon atoms, said odourant being present in amount sufficient to warn that the composition is not a beverage suitable for drinking.

2. A composition according to claim 1 having a pH in the range 1 to 5.

3. A composition according to claim 1 which further comprises a surface active agent.

4. A composition according to claim 1 wherein the salt of the herbicidal bipyridylium quaternary cation is a compound of the formula:

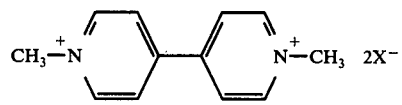

wherein X is an anion.

5. A composition according to claim 1 wherein the amount of the herbicidal bipyridylium cation present in the composition is from 50 to 300 grams per liter.

6. A composition according to claim 1 wherein the alkyl carboxylic acid used as the odourant is a compound selected from the group consisting of n-valeric, iso-, and n-butyric acid.

7. A composition according to claim 1 wherein the odourant is present in the proportion of from 0.5 to 5% by weight of the composition.

* * * * *